US010966883B2

(12) United States Patent
Ehrnsperger et al.

(10) Patent No.: US 10,966,883 B2
(45) Date of Patent: Apr. 6, 2021

(54) ABSORBENT CORE HAVING TUBE-SHAPED SWELLING CHAMBER

(71) Applicant: The Procter & Gamble Company, Cincinnati, OH (US)

(72) Inventors: Bruno Johannes Ehrnsperger, Bad Soden (DE); Christine Elisabeth Zipf, Lauds-Konigshofen (DE); Andrea Peri, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 330 days.

(21) Appl. No.: 15/639,285

(22) Filed: Jun. 30, 2017

(65) Prior Publication Data

US 2018/0008486 A1    Jan. 11, 2018

Related U.S. Application Data

(60) Provisional application No. 62/358,185, filed on Jul. 5, 2016, provisional application No. 62/402,388, filed on Sep. 30, 2016.

(51) Int. Cl.
*A61F 13/534* (2006.01)
*A61F 13/53* (2006.01)
(Continued)

(52) U.S. Cl.
CPC ...... *A61F 13/534* (2013.01); *A61F 13/15203* (2013.01); *A61F 13/49017* (2013.01);
(Continued)

(58) Field of Classification Search
None
See application file for complete search history.

(56) References Cited

U.S. PATENT DOCUMENTS 3,848,594 A    11/1974    Buell
3,860,003 A    1/1975    Buell
(Continued)

FOREIGN PATENT DOCUMENTS

EP    149880    7/1985
EP    1013252 B1    6/2000
(Continued)

OTHER PUBLICATIONS

International Search Report, PCT/US2017/040399, dated Sep. 22, 2017, 14 pages.

*Primary Examiner* — Shawn Mckinnon
(74) *Attorney, Agent, or Firm* — Wednesday G. Shipp

(57) ABSTRACT

An absorbent cores includes absorbent material enclosed a core wrap which comprises a liquid permeable substrate layer. The core contains from about 87% to about 100% of superabsorbent polymer and a tube-shaped swelling chamber having a length to width aspect ratio of less than or equal to about 5:1. The area of the core is at least twice the area of the swelling chamber, and the core contains a water responsive immobilizing agent to immobilize the superabsorbent polymer prior to water insult. The tube-shaped swelling chamber is a portion of the absorbent core containing superabsorbent polymer that is delimited by a plurality of continuous permanent seals that each join together overlapping portions of the core wrap and prevent superabsorbent polymer from moving across the seals.

16 Claims, 8 Drawing Sheets

(51) Int. Cl.
  *A61F 13/539* (2006.01)
  *A61F 13/15* (2006.01)
  *A61F 13/49* (2006.01)

(52) U.S. Cl.
  CPC ............ *A61F 13/53* (2013.01); *A61F 13/539* (2013.01); *A61F 2013/15406* (2013.01); *A61F 2013/15463* (2013.01); *A61F 2013/5349* (2013.01); *A61F 2013/530481* (2013.01); *A61F 2013/530489* (2013.01); *A61F 2013/530562* (2013.01); *A61F 2013/53933* (2013.01)

(56) References Cited

U.S. PATENT DOCUMENTS

| | | |
|---|---|---|
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievet et al. |
| 4,573,986 A | 3/1986 | Minetola et al. |
| 4,609,518 A | 9/1986 | Curro et al. |
| 4,629,643 A | 12/1986 | Curro et al. |
| 4,662,875 A | 5/1987 | Hirotsu et al. |
| 4,681,793 A | 7/1987 | Linman et al. |
| 4,695,278 A | 9/1987 | Lawson |
| 4,699,622 A | 10/1987 | Toussant |
| 4,710,189 A | 12/1987 | Lash |
| 4,731,066 A | 3/1988 | Korpman |
| 4,785,996 A | 11/1988 | Ziecker et al. |
| 4,795,454 A | 1/1989 | Dragoo |
| 4,808,178 A | 2/1989 | Aziz |
| 4,842,666 A | 6/1989 | Werenicz |
| 4,846,815 A | 7/1989 | Molloy |
| 4,886,509 A | 12/1989 | Mattsson |
| 4,894,060 A | 1/1990 | Nestegard |
| 4,909,803 A | 3/1990 | Aziz et al. |
| 4,946,527 A | 8/1990 | Battrell |
| 4,963,140 A | 10/1990 | Robertson et al. |
| 5,006,394 A | 4/1991 | Baird |
| 5,102,597 A | 4/1992 | Roe et al. |
| 5,137,537 A | 8/1992 | Herron et al. |
| 5,149,334 A | 9/1992 | Roe et al. |
| 5,151,092 A | 9/1992 | Buell et al. |
| 5,180,622 A | 1/1993 | Berg et al. |
| 5,221,274 A | 6/1993 | Buell et al. |
| 5,242,436 A | 9/1993 | Weil et al. |
| 5,300,565 A | 4/1994 | Berg et al. |
| 5,492,962 A | 2/1996 | Lahrman et al. |
| 5,499,978 A | 3/1996 | Buell et al. |
| 5,507,736 A | 4/1996 | Clear et al. |
| 5,549,791 A | 8/1996 | Herron et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,601,542 A | 2/1997 | Melius et al. |
| 5,607,760 A | 3/1997 | Roe |
| 5,609,587 A | 3/1997 | Roe |
| 5,643,588 A | 7/1997 | Roe et al. |
| 5,700,254 A | 12/1997 | McDowall et al. |
| 5,714,156 A * | 2/1998 | Schmidt ............... A61L 15/225 424/404 |
| 5,865,823 A | 2/1999 | Curro |
| 5,938,648 A | 8/1999 | Lavon et al. |
| 5,968,025 A | 10/1999 | Roe et al. |
| 6,004,306 A | 12/1999 | Robles et al. |
| 6,306,123 B1 | 10/2001 | Salerno et al. |
| 6,432,098 B1 | 8/2002 | Kline et al. |
| 6,610,900 B1 | 8/2003 | Tanzer |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,716,441 B1 | 4/2004 | Roe et al. |
| 6,863,933 B2 | 3/2005 | Cramer et al. |
| 6,946,585 B2 | 9/2005 | Brown |
| 6,965,058 B1 | 11/2005 | Raidel et al. |
| 7,112,621 B2 | 9/2006 | Rohrbaugh et al. |
| 7,297,395 B2 | 11/2007 | Kainth et al. |
| 7,744,576 B2 | 6/2010 | Busam et al. |
| 7,786,341 B2 | 8/2010 | Schneider et al. |
| 8,148,598 B2 | 4/2012 | Tsang et al. |
| 9,066,835 B2 | 6/2015 | Okawa et al. |
| 9,216,118 B2 * | 12/2015 | Roe ....................... A61F 13/537 |
| 9,707,135 B2 | 7/2017 | Sheldon et al. |
| 2003/0014038 A1 | 1/2003 | Fine |
| 2003/0105190 A1 | 6/2003 | Diehl et al. |
| 2003/0148684 A1 | 8/2003 | Cramer et al. |
| 2005/0008839 A1 | 1/2005 | Cramer et al. |
| 2006/0024433 A1 | 2/2006 | Blessing et al. |
| 2007/0118087 A1 | 5/2007 | Flohr et al. |
| 2008/0312617 A1 | 12/2008 | Hundorf et al. |
| 2008/0312622 A1 | 12/2008 | Hundorf et al. |
| 2010/0051166 A1 | 3/2010 | Hundorf et al. |
| 2011/0250413 A1 | 10/2011 | Lu et al. |
| 2011/0268932 A1 | 11/2011 | Catalan et al. |
| 2011/0319848 A1 | 12/2011 | McKiernan et al. |
| 2012/0232508 A1 | 9/2012 | Urushihara |
| 2012/0312491 A1 | 12/2012 | Jackels et al. |
| 2012/0316526 A1 | 12/2012 | Rosati et al. |
| 2015/0045756 A1 * | 2/2015 | Wright ............... B01J 20/28016 604/366 |
| 2015/0164699 A1 | 6/2015 | Schmitz |
| 2015/0174857 A1 | 6/2015 | Christoph |
| 2015/0080822 A1 | 9/2015 | Ehrnsperger et al. |
| 2015/0342799 A1 | 12/2015 | Michiels et al. |
| 2016/0074250 A1 | 3/2016 | Strube et al. |

FOREIGN PATENT DOCUMENTS

| | | |
|---|---|---|
| WO | WO 95/10996 | 4/1995 |
| WO | WO 95/16746 | 6/1995 |
| WO | WO 95/24173 | 9/1995 |
| WO | WO 95/34329 | 12/1995 |
| WO | WO 2000/59430 | 10/2000 |
| WO | WO 02/064877 | 8/2002 |
| WO | WO 02/067809 | 9/2002 |
| WO | WO 2006/083584 | 8/2006 |
| WO | WO 2007/046052 | 4/2007 |
| WO | WO 2007/047598 | 4/2007 |
| WO | WO 2009/155264 | 12/2009 |
| WO | WO 2009/155265 | 12/2009 |
| WO | WO 2011/163582 | 12/2011 |
| WO | WO 2012/170778 | 12/2012 |
| WO | WO 2012/174026 | 12/2012 |

\* cited by examiner

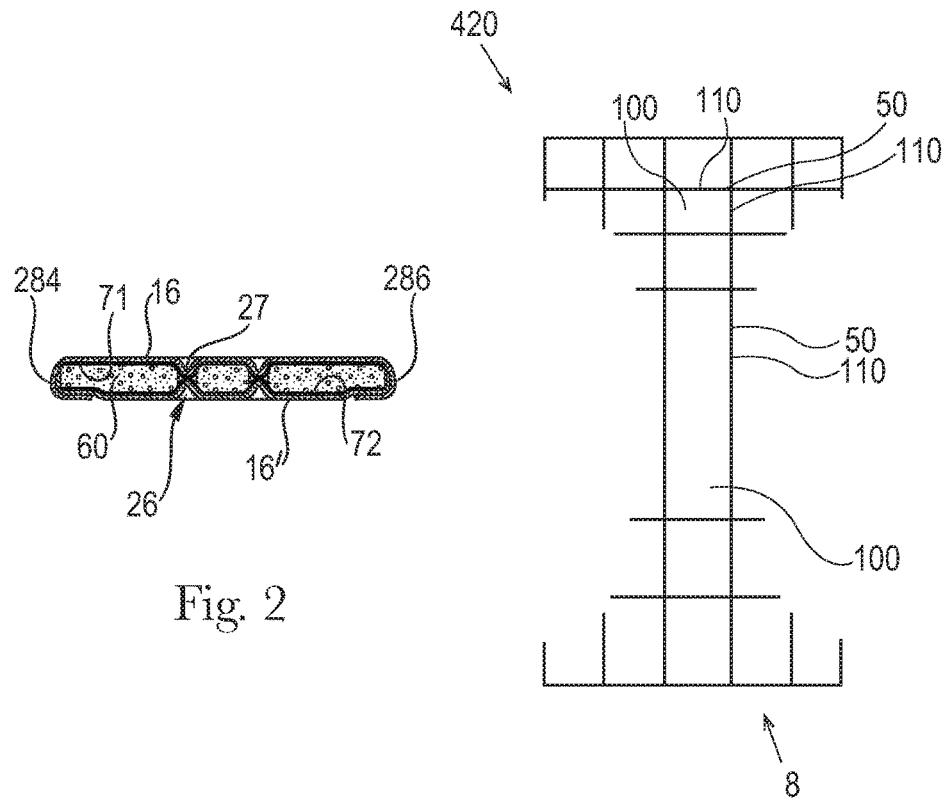
Fig. 2
Fig. 3
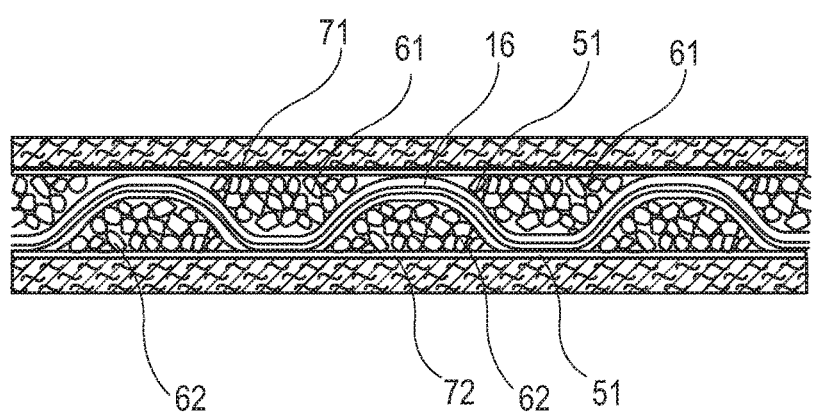
Fig. 4

ABSORBENT CORE HAVING TUBE-SHAPED SWELLING CHAMBER

FIELD OF THE INVENTION

The disclosure relates to absorbent cores containing superabsorbent polymers (SAP) for use in wearable absorbent hygiene articles that absorb and contain body exudates of the wearer, the cores having a tube-shaped swelling chamber that influences the movement of the SAP after wetting.

BACKGROUND OF THE INVENTION

Wearable absorbent hygiene articles typically include absorbent cores that absorb and contain body exudates, e.g. urine or menstrual blood, of the wearer. The core absorbs and retains the exudate until a new article may be applied to the wearer. The core may contain SAP, cellulose-containing fibers, or both. Typically, the use of relatively more fiber versus SAP results in a thicker core, and the use of relatively more SAP versus fiber results in a thinner core.

Where significant amounts of SAP are used, a phenomenon known as gel-blocking may occur after liquid insult. Gel-blocking refers to a situation where SAP particles deform during swelling and block the interstitial spaces between the particles, or between the particles and fibers (if present), thus inhibiting the flow of liquid through the interstitial spaces. Another concern that may occur where significant amounts of SAP are used is known as sagging. This refers to a situation where SAP absorbs and retains an amount of liquid weighing many times its own weight, and this increased weight in the absorbent core is pulled by gravity, e.g. when the wearer is crawling or standing, and causes a bunching up of material in the crotch area of the absorbent article. Due to the weight of the bunched up material, the absorbent article sags and may even pull away from the wearer. Yet another concern is that the crotch area may become very bulky after wetting. As SAP is often placed at or near the point of urination in order to quickly absorb gushes of urine, and such areas tend to be in the medial and frontal areas of the crotch, once these areas are wetted, they tend to bulk up, due to the SAP swelling as it absorbs and retains liquid.

U.S. Pat. No. 6,610,900 (Tanzer) discloses an absorbent article having a selectively stretchable absorbent composite between a topsheet and a backsheet, the absorbent composite having a selectively stretchable substrate layer and a plurality of pockets in or on the substrate layer. The pockets each contain a quantity of superabsorbent material, which can swell when exposed to liquid insult. When the substrate is stretched, the pockets become spaced further apart, alleviating gel blocking caused by adjacent pockets swelling toward each other. This involves discrete pockets containing SAP, but they are sealed and although the pockets can swell and stretch after wetting, they do not allow for post-wetting movement of SAP outside of the pocket.

US 2015/0174857A1 (Schmitz) discloses free flowing materials sandwiched between web materials, the web materials being bonded to each other at bonding points, which define bonding regions which delimit the accumulation regions in which the free flowing material is positioned. This involves discrete pockets, where permanently bonded pocket comprises two smaller compartments divided by a non-permanent bond—one compartment containing SAP, the other empty. Upon wetting, the non-permanent bond is broken and the SAP can occupy the previously empty compartment.

The inventors have found that it is advantageous to move wetted SAP through the use of a tube-shaped chamber from its original (dry) position in the core. The inventors have found that it is desirable to move SAP in a one-way (unidirectional) manner, away from the crotch, but not in the opposite direction, towards the crotch, and that it is desirable to provide a core with a geometry that helps achieve this, particularly in the context of cores containing significant amounts of SAP, perhaps even being free or substantially free of cellulosic material. Further, we have found that it is desirable to provide a core that enables one-way movement of wetted gel by at least a certain distance, yet it provides good dry immobilization of the SAP prior to liquid insult, thus, inhibiting dry SAP from moving around within the core, so it is at the proper place to receive liquid insult, but once wetted, the wetted SAP moves away from the center of the crotch so that it does not build up and create sagging, and/or reduces gel blocking. Without being bound by theory, it is believed that the cores of the present invention solve one or more of the aforementioned problems.

SUMMARY OF THE INVENTION

Disclosed are absorbent cores comprising a core wrap enclosing absorbent material, wherein the core wrap comprises a liquid permeable substrate layer and the absorbent material may comprise from about 87% to about 100% of superabsorbent polymer. The core further comprises a tube-shaped swelling chamber, the swelling chamber having a length to width aspect ratio of less than or equal to about 5:1. The area of the core may be at least twice the area of the swelling chamber. The tube-shaped swelling chamber is a portion of the absorbent core containing superabsorbent polymer that is delimited by a plurality of continuous permanent seals that each join together overlapping portions of the core wrap and prevent superabsorbent polymer from moving across the seals.

BRIEF DESCRIPTION OF THE DRAWINGS

FIG. 2 is a cross sectional view of the absorbent core shown in FIG. 1 taken perpendicular to the longitudinal axis at the crotch point, C'.

FIG. 3 is a partial plan view of a portion of an exemplary absorbent core layer.

FIG. 4 is a partial cross sectional view of an exemplary absorbent core.

DETAILED DESCRIPTION OF THE INVENTION

Definitions

Figure 1:
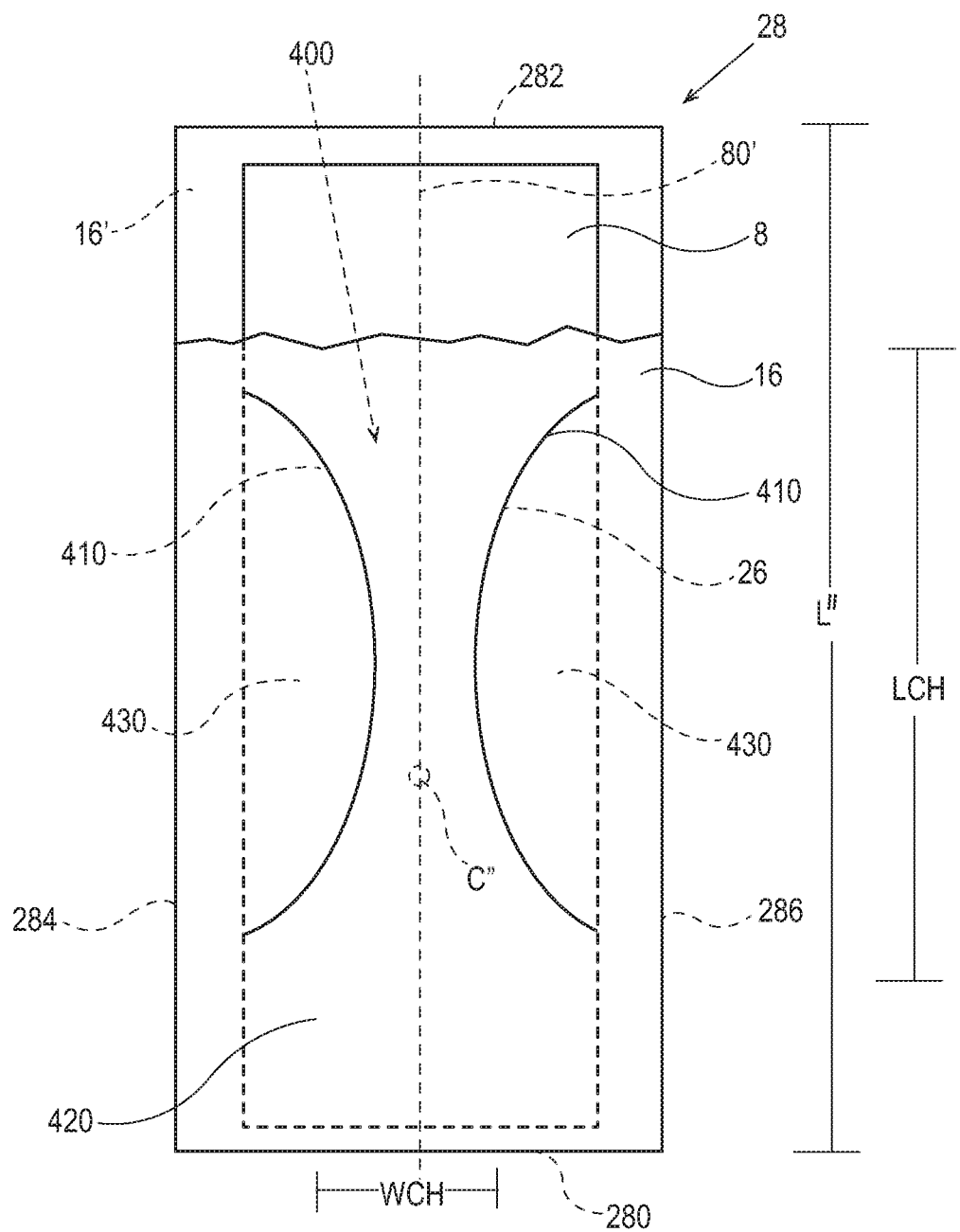
FIG. 1 is a plan view of an exemplary absorbent core.

The following term explanations may be useful in understanding the present disclosure.

As used herein, "absorbent articles" and "absorbent articles for personal hygiene" refer to disposable devices such as baby diapers, infant training pants, adult incontinence products or feminine hygiene sanitary pads, and the like which are placed against or in proximity to the body of the wearer to absorb and contain exudates discharged from the body. The absorbent articles of the invention will be further illustrated in the below description and in the Figures in the form of a taped diaper. Nothing in this description should be however considered limiting the scope of the claims unless explicitly indicated otherwise.

A "nonwoven web" as used herein means a manufactured sheet, web or batting of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

Absorbent Cores

The absorbent cores of the invention will be typically made to be used in an absorbent article. The absorbent core may for example be made on-line and assembled directly with the remaining components of the article or may be off-line at another site and transported to the converting line. It is also possible to use the absorbent core directly as an absorbent article without further assembling of other components for applications which do not require other layers. Typically however the absorbent core will be assembled with other components such as a topsheet and a backsheet to form a finished absorbent article, as will be described further below using a diaper as an example. The absorbent core may be generally rectangular or may be shaped. In certain embodiments, the absorbent core is substantially hour-glass shaped, in the longitudinal direction. In further embodiments, the absorbent material deposition area (discussed below) may be shaped, and may be substantially hour-glass shaped.

The absorbent core is typically the component of the article having the most absorbent capacity. The absorbent core of the invention comprises a core wrap enclosing an absorbent material, and may also comprise at least one adhesive. The absorbent material comprises SAP. The absorbent material may comprise relatively high amounts of SAP enclosed within the core wrap. By "absorbent material" it is meant a material which has some absorbency property or liquid retaining properties, such as SAP, cellulosic fibers as well as synthetic fibers. Typically, adhesives used in making absorbent cores have no absorbency properties and are not considered as absorbent material.

The SAP content may represent at least about 87% or more (in particular at least about 90%, at least about 95%, at least about 98%, and up to 100%) by weight of the absorbent material enclosed in the core wrap. The core wrap itself is not considered as absorbent material for the purpose of assessing the percentage of SAP in the absorbent core. A relatively high amount of SAP will provide a relatively thin core compared to conventional core typically comprising between 40-60% by weight of cellulosic material. The absorbent core may be thin, for example having a thickness not exceeding 5 mm, e.g. from 0.2 mm to 4 mm, in particular from 0.5 to 3 mm, as measured with the Dry Absorbent Core Caliper Test disclosed herein.

As discussed above, the inventors have found that it is advantageous to move wetted SAP at least a certain distance from its original (dry) position in the core in the longitudinal direction or the transverse direction (not in the thickness direction). Without being bound by theory, it is believed that the cores of the present invention are designed to restrict the swelling space available to SAP (in the thickness direction), thus urging it to move or flow (in the longitudinal and/or transverse directions). To achieve flow (in the transverse or longitudinal direction) of the swollen SAP, there should not only be provided an urge to flow (stress) via restricting the swelling space as explained above, but also the swollen SAP should be capable of moving relatively easily ("flowing", e.g. having low viscosity, and/or low or no yield stress). This may be achieved, e.g., by avoiding (a) mechanical entanglement of the swollen SAP particles, (b) SAP particles not sticking to each other, (c) SAP particles not sticking to something else in the core, and/or (d) allowing SAP particles to move in the desired direction by not having wall/restrictions in that direction.

Mechanical entanglement can be avoided, e.g. by (a) having the appropriate swollen SAP particle morphology, smooth and round leading to less entanglement; (b) not having other materials (such as pulp fibers or other fibers) blended with the SAP particles that promote entanglement; (c) having the particles loosely packed (rather than compacted); and/or (d) not compressing the gel bed too much. The skilled person will recognize that even for easily flowable gels there is a delicate balance between restricting the swelling space in the z-direction and correspondingly compressing the gel bed a bit creating the stress that will cause the gel to move, and not restricting the swell space in the z-direction too much such that the gel bed is compressed so much that the gel particles mechanically entangle and no longer flow. The inventors found this balance by (a) using core wrap materials that have the right stress strain behaviors, and by (b) using the right geometries.

Swollen gel particles sticking together can be avoided, e.g., by (a) having particles that have non-tacky surfaces when wet (tacky gels would e.g. be superabsorbent gels that both have a cationic and an anionic polymer (such as the mixed bed ion exchange SAP's), (b) not adding high viscosity water soluble fluids (such as glycerine) to the gel bed, and/or (c) avoiding that when the urine evaporates the particles are under pressure and the salts from the urine "bake" the particles together.

Avoiding that particles stick to something else can be achieved, e.g. by (a) not having (fibrous) glue to immobilize the gel particles, (b) having a water solvable glue or other water responsive agent to immobilize the dry gel particles that will dissolve or otherwise deteriorate in the presence of urine and not immobilize the wetted gel particles, and/or (c) not having other tacky when wet material blended with the gel or adjacent to the gel.

This may be also be achieved by having low or no adhesive gluing the SAP to the core, including flowable (or non-sticky) SAP in the core, providing a geometry in the core that does not allow wetted SAP movement in certain directions (e.g. placement of walls, barriers, permanent seams, etc.), and combinations thereof. Additionally, the cores of the present invention may provide the opportunity for swelled SAP to move in a guided direction. This may be achieved by having open areas beyond such walls, barriers, permanent seams, etc. that the wetted SAP may "flow" to. The skilled person will appreciate that the cores do not actually actively move the wetted SAP, rather, the movement of SAP should be viewed as dry SAP incurring a wetness insult, then swelling as it absorbs the wetness, then the swollen SAP encountering resistance from its surroundings, e.g. walls, barriers, permanent seams, etc., and accordingly, "moving" towards areas of less resistance.

An exemplary absorbent core 28 of the invention is shown in isolation in FIGS. 1-2 and will now be further described. The absorbent core shown and its description are purely for exemplary purpose and are not intended to limit the scope of the claims, unless otherwise stated. The absorbent core typically comprises a front side 280, a back side 282 and two longitudinal sides 284, 286 joining the front side 280 and the back side 282. The absorbent core also comprises a generally planar top side 16 and a generally planar bottom side 16' formed by the core wrap. The front side 280 of the core is the side of the core intended to be placed towards the front edge 10 of the absorbent article. The core may have a longitudinal axis 80' corresponding substantially to the longitudinal axis of the article 80, as seen from the top in a planar view as in FIG. 1. Typically the absorbent material will be advantageously distributed in higher amount towards the front side and middle portion of the core than towards the back side as more absorbency is required at the front. Typically the front and back sides of the core are shorter than the longitudinal sides of the core. The core wrap may be formed by two nonwoven materials which may be at least partially sealed along the sides of the absorbent core. The first nonwoven may substantially form the whole of the top side of the core wrap and the second nonwoven substantially the whole of the bottom side 16' of the core wrap. The top side and first nonwoven are represented by the same number 16 on the drawings, the bottom side and the second nonwoven by number 16'. The core wrap may be at least partially sealed along its front side, back side and/or two longitudinal sides to improve the containment of the absorbent material during use.

The absorbent material may in particular comprise less than 10% weight percent of natural or synthetic fibers, or less than 5% weight percent, or even be substantially free of natural and/or synthetic fibers. The absorbent material may advantageously comprise little or no airfelt (cellulose) fibers, in particular the absorbent core may comprise less than 15%, 10%, 5% airfelt (cellulose) fibers by weight of the absorbent core, or even be substantially free of cellulose fibers.

The absorbent core 28 comprises at least one swelling chamber 400 delimited by permanent continuous seals 410. When wetted, absorbent material may become mobile within an internal chamber zone 420. The continuous permanent seals 410 prevent absorbent material from passing from the internal chamber zone 420 into external zone 430. In such external zones 430, the absorbent material may be immobilized in its wet state, or the zone 430 may be free or substantially free of superabsorbent polymer, or the absorbent material may be mobile but flow differently than absorbent material within the internal chamber zone.

The length L" of the absorbent core as measured along it axis 80' from the front side 280 to the back side 282 should be adapted for the intended article in which it will be used. The absorbent cores may typically have a length from 150 mm to 500 mm, and a width from 40 mm to 150 mm.

The core may comprise one or more adhesives as discussed below. In some embodiments, the core may comprise about 25% or less, or about 20% or less, or about 15% or less, or from about 0.5% to about 20%, or from about 1% to about 15%, or from about 4% to about 13%, or from about 2% to about 10% of adhesive based on the total weight of the core, reciting for each range every 1% increment therein. The individual components of the absorbent core will now be described in further detail.

Core Wrap (16, 16')

The function of the core wrap is to enclose the absorbent material. Typical core wraps comprise two substrates 16, 16' which are attached to another, but the core wrap may also be made of a single substrate folded around the absorbent material, or may comprises several substrates. When two substrates are used, these may be typically attached to another along at least part of the periphery of the absorbent core. Typical attachments are the so-called C-wrap and sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing. In a sandwich wrap, the edges of both substrates are attached, e.g. by gluing, to another in a flat configuration.

The core wrap may be formed by any materials suitable for enclosing the absorbent material. Typical substrate materials used in the production of conventional cores may be used, in particular nonwovens but also paper, tissues, films (including apertured or perforated films), mesh, wovens, or laminate of any of these. The core wrap material may comprise any suitable basis weight. In nonlimiting examples, the substrate material may have a basis weight of at least about 5 gsm, or at least about 8 gsm, or at least about 10 gsm, or from about 5 gsm to about 30 gsm, or from about 8 gsm to about 25 gsm, reciting for each range every 1 gsm increment therein. In other nonlimiting examples, the substrate material may have a basis weight of about 60 gsm or greater, or about 70 gsm or greater, or about 80 gsm or greater. The basis weight and type of material can be selected to ensure the right stress strain profile for the invention.

The core wrap may in particular be formed by a nonwoven web, such as a carded nonwoven, a spunbond nonwoven ("S") or a meltblown nonwoven ("M"), and laminates of any of these. For example spunmelt polypropylene nonwovens are suitable, in particular those having a laminate web SMS, or SMMS, or SSMMS, structure. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP. Elastic fibers may be used as well. Suitable substrates may be elastomeric. In particular, the substrate on the garment-facing side of the absorbent core may be elastomeric. In such instances, it may be advantageous to partially attach such elastomeric layer to the backsheet to ensure the desired extensibility in the final product.

The core wrap may be liquid permeable. If the core wrap comprises a first substrate 16 and a second substrate 16' these may be made of the same type of material, or may be made of different materials or one of the substrate may be treated differently than the other to provide it with different properties. One or both of the substrates may comprise a liquid permeable layer. As some of the polymers used for nonwoven production are inherently hydrophobic, they are preferably coated with hydrophilic coatings if placed on the fluid receiving side of the absorbent core. It may be advantageous that the top side 16 of the core wrap, i.e. the side placed closer to the wearer in the absorbent article, be more hydrophilic than the bottom side 16' of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Permanently hydrophilic nonwovens are also useful in some embodiments. Surface tension can be used to measure how permanently a certain hydrophilicity level is achieved. Liquid strike through can be used to measure the hydrophilicity level. The first and/or second substrate may in particular have a surface tension of at least 55, preferably at least 60 and most preferably at least 65 mN/m or higher when being wetted with saline solution. The substrate may also have a liquid strike through time of less than 5 seconds for a fifth gush of liquid. These values can be measured using the test methods described in U.S. Pat. No. 7,744,576B2 (Busam et al.): "Determination Of Surface Tension" and "Determination of Strike Through" respectively.

Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The substrate may have for example an air-permeability of from 40 or from 50, to 300 or to 200 $m^3/(m^2 \times min)$, as determined by EDANA method 140-1-99 (125 Pa, 38.3 $cm^2$). The material of the core wrap may alternatively have a lower air-permeability, e.g. being non-air-permeable, for example to facilitate handling on a moving surface comprising vacuum.

The core wrap may be sealed along its longitudinal edges and/or its transversal edges. In a C-wrap configuration, for example, a first substrate 16 may be placed on one side of the core and extends around the core's longitudinal edges to partially wrap the opposed bottom side of the core (see FIG. 2). The second substrate 16' is typically present between the wrapped flaps of the first substrate 16 and the absorbent material 60. The flaps of the first substrate 16 may be glued to the second substrate 16' to provide a strong seal. This so called C-wrap construction can provide benefits such as improved resistance to bursting in a wet loaded state compared to a sandwich seal. The front side and back side of the core wrap may then also be sealed for example by gluing the first substrate and second substrate to another to provide complete enclosing of the absorbent material across the whole of the periphery of the core. For the front side and back side of the core the first and second substrate may extend and be joined together in a substantially planar direction, forming for these edges a so-called sandwich construction. In the so-called sandwich construction, the first and second substrates may also extend outwardly on all sides of the core and be sealed flat along the whole or parts of the periphery of the core typically by gluing and/or heat/pressure bonding. Typically neither first nor second substrates need to be shaped, so that they can be rectangularly cut for ease of production but of course other shapes are possible.

The terms "seal" and "enclosing" are to be understood in a broad sense. The seal does not need to be continuous along the whole periphery of the core wrap but may be discontinuous along part or the whole of it, such as formed by a series of seal points spaced on a line. Typically a seal may be formed by gluing, thermal bonding, ultrasonic bonding, and/or pressure bonding/crimping. The core wrap may also be formed by a single substrate which may enclose the absorbent material as in a parcel wrap and be for example sealed along the front side and back side of the core and one longitudinal seal.

Absorbent Material 60

The absorbent core 28 comprises an absorbent material 60 comprising SAP. The absorbent material may be for example applied as a continuous layer. The absorbent material may also be comprised of individual pockets or stripes of absorbent material enclosed within the core wrap.

The absorbent material may be disposed within frangible pockets 100 as shown in FIG. 3. In certain embodiments, the internal chamber zone 420 comprises absorbent material disposed in frangible pockets 100 in a dry state. The pockets may be substantially surrounded by circumscribing bonds 110 (depicted as the grid-like lines in FIG. 3) formed by water responsive immobilizing agents 50, which water responsive agents may be selected from the group consisting of: adhesive bonds, water soluble bonds, bonds formed by heat fusion, ultrasound, pressure, mechanical, or crimping, and combinations thereof. The bonds may be water responsive, i.e., weaken or deteriorate upon exposure to water, in particular at least 5 ml of water. The circumscribing bonds may join the top substrate layer 16 to the bottom substrate layer 16' prior to liquid insult.

The absorbent material may otherwise be immobilized by water responsive immobilizing agents, in forms other than frangible pockets. In some embodiments, the water responsive immobilizing agent may be in the form of fibers, such as a fibrous water soluble adhesive.

In some embodiments, a continuous layer of absorbent material, in particular of SAP, may also be obtained by combining two absorbent layers having matching discontinuous absorbent material application pattern wherein the resulting layer is substantially continuously distributed across the absorbent particulate polymer material area, as taught in US2008/0312622A1 (Hundorf) for example. In this way, each absorbent material layer comprises a pattern having absorbent material areas and absorbent material-free areas, wherein the absorbent material areas of the first layer correspond substantially to the absorbent material-free areas of the second layer and vice versa. A microfibrous glue 51 as disclosed further below may optionally be applied on a portion of each absorbent material layer to immobilize it on each substrate. The microfibrous glue 51 may be applied, for example, in the external zone 430.

As exemplary shown in FIG. 4, a portion of the absorbent core 28 may thus comprise a first absorbent layer and a second absorbent layer, the first absorbent layer comprising a first substrate 16 and a first layer 61 of absorbent material, which may be 100% SAP, and the second absorbent layer comprising a second substrate 16' and a second layer 62 of absorbent material, which may also be 100% SAP. The first and second SAP layers may be applied as transversal stripes or "land areas" having the same width as the desired absorbent material deposition area 8 on their respective substrate before being combined. The stripes may advantageously comprise different amount of absorbent material to provide a profiled basis weight along the longitudinal axis and/or transversal axis of the core 80'. The first substrate 16 and the second substrate 16' may form the core wrap. An auxiliary glue 71, 72 may be applied between one or both substrates and the absorbent layers, as well as microfiber glue on each absorbent layer.

Superabsorbent Polymer Particles (SAP)

"Superabsorbent polymers" as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). These polymers are typically used in particulate forms ("SAP") so as to be flowable in the dry state. The term "particles" refers to granules, fibers, flakes, spheres, powders, platelets and other shapes and forms known to persons skilled in the art of superabsorbent polymer particles.

Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. The superabsorbent polymers can be internally cross-linked, i.e. the polymerization is carried out in the presence of compounds having two or more polymerizable groups which can be free-radically copolymerized into the polymer network. Exemplary superabsorbent polymer particles of the prior art are for example described in WO2006/083584, WO2007/047598, WO2007/046052, WO2009/155265, WO2009/155264.

At least some of the superabsorbent polymers may be present in the form of agglomerated superabsorbent polymer particles. Agglomerated superabsorbent polymer particles comprise agglomerated precursor particles having a first mass average particle size, and wherein the agglomerated superabsorbent polymer particles have a second mass average particle size which is at least 25% greater than the first mass average particle size. The second mass average particle size may be at least 30%, or at least 40% or at least 50% higher than the first mass average particle size.

The agglomerated superabsorbent polymer particles may be obtained by various methods. Agglomerated particles may be for example obtained by aggregating the precursor particles with an interparticle crosslinking agent reacted with the polymer material of the precursor particles to form crosslink bonds between the precursor particles have been for example disclosed in U.S. Pat. Nos. 5,300,565, 5,180, 622, (both to Berg), U.S. Pat. Nos. 5,149,334, 5,102,597 (both to Roe), U.S. Pat. No. 5,492,962 (Lahrman). Agglomerated superabsorbent polymer particles may also be obtained by a method comprising the steps of providing superabsorbent polymer particles and mixing the superabsorbent polymer particles with a solution comprising water and a multivalent salt having a valence of three or higher. This method is further disclosed in EP14168064.

The superabsorbent polymer particles of the core of the invention may in particular comprise at least 10%, or at least 20% or at least 30% or at least 50% by weight of the agglomerated superabsorbent polymer particles.

The total amount of SAP present in the absorbent core may also vary according to expected user of the article. Diapers for newborns require less SAP than infant or adult incontinence diapers. In nonlimiting examples, the absorbent core may comprise from about 2 to about 50 g, or about 3 to about 40 g, or 5 to about 25 g, or from about 6 g to about 20 g, or from about 8 g to about 15 g, of superabsorbent polymer, reciting for every range each 2 g increment therein. The average SAP basis weight within the (or "at least one", if several are present) deposition area 8 of the SAP may be for example of at least about 100, 200, 300, 400, 500, 700 or more, or about 1000 or less, or about 900 or less g/m$^2$. The material free areas 26 present in the absorbent material deposition area 8 are deducted from the absorbent material deposition area to calculate this average basis weight.

The Ball Breakthrough (BB) value of a swollen layer of the SAP composition can provide a measure of the integrity of the layer of the SAP composition in the swollen state, which may provide a measure of the SAP's stickiness, or conversely, its ability to flow. The BB is the force (peak load, in grams force) required to rupture a layer of an SAP composition that is swollen in synthetic urine solution, under specific conditions. In a Ball Breakthrough measurement, a 1.0 g sample of the absorbent polymer composition is allowed to absorb 30 mL of synthetic urine solution to form a swollen gel layer. The force required to rupture the layer with a ball-shaped stainless steel probe is the Ball Breakthrough of the material. The method for determining Ball Breakthrough of SAP's is described in detail in the Test Methods section below. As is discussed above, a relatively low Ball Breakthrough indicates good flowability of a layer comprising a high concentration of SAP.

SAP's for use in the present invention may be described in terms of their ability to exhibit an integrity that allows flowability in the swollen state. In this regard, such SAP's may exhibit a BB from 0 gf to 50 gf, preferably from 0 gf to 25 gf. Good integrity of the SAP may be achieved, e.g. by varying certain ingredients/processes of an SAP to make it more flowable. Additionally or alternatively, SAP may have a value of absorption against pressure (AAP) of about 15 g/g or more, and/or about 45 g/g or less, or from about 15 g/g to about 45 g/g, or from about 20 g/g to about 40 g/g as measured with an Absorption Against Pressure Test Method, reciting for each range every 5 g/g increment therein.

Absorbent Material Deposition Area 8

The absorbent material deposition area 8 can be defined by the periphery of the layer formed by the absorbent material 60 within the core wrap, as seen from the top side of the absorbent core. The absorbent material deposition area 8 can be generally rectangular, for example, but other shapes can also be used such as a "T" or "Y" or "sand-hour" or "dog-bone" shape. In particular the deposition area may show a tapering along its width towards the middle or "crotch" region of the core. In this way, the absorbent material deposition area may have a relatively narrow width in an area of the core intended to be placed in the crotch region of the absorbent article. This may provide for example better wearing comfort. The absorbent material deposition area 8 may thus have a minimum width (as measured in the transversal direction) at its narrowest point which is less than about 100 mm, 90 mm, 80 mm, 70 mm, 60 mm or even less than about 50 mm. This minimum width may further be for example at least 5 mm, or at least 10 mm, smaller than the maximum width of the deposition area at its widest point in the front and/or back regions of the deposition area 8. The deposition area may be segmented; for instance, portions may comprise absorbent material immobilized with water responsive immobilizing agents and portions may comprise absorbent material immobilized with materials that do not deteriorate or detach upon exposure to water (e.g., thermoplastic adhesive).

The basis weight (amount deposited per unit of surface) of the SAP may also be varied along the deposition area 8 to create a profiled distribution of absorbent material, in particular SAP, in the longitudinal direction, in the transversal direction, or both directions of the core. Hence along the longitudinal axis of the core, the basis weight of absorbent material may vary, as well as along the transversal axis, or any axis parallel to any of these axes. The basis weight of SAP in area of relatively high basis weight may thus be for example at least 10%, or 20%, or 30%, or 40%, or 50% higher than in an area of relatively low basis weight. In particular the SAP present in the absorbent material deposition area at the longitudinal position of the crotch point C' may have more SAP per unit of surface deposited as compared to another area of the absorbent material deposition area 8, particularly in a dry state.

The absorbent material may be deposited using known techniques, which may allow relatively precise deposition of SAP at relatively high speed. In particular the SAP printing technology as disclosed for example in US2006/024433 (Blessing), US2008/0312617 and US2010/0051166A1 (both to Hundorf et al.) may be used. This technique uses a transfer device such as a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate in particular to provide one or more area(s) 26 substantially free of absorbent material surrounded by, or adjacent to, absorbent material. The areas substantially free of absorbent material can be formed for example by modifying the pattern of the grid and receiving drums so that no SAP is applied in the selected areas, as exemplary disclosed in US2012/0312491 (Jackels). In nonlimiting examples, the areas 26 substantially free of absorbent material may coincide with permanent seal(s) 410 forming swelling chambers 400.

Area(s) 26 Substantially Free of Absorbent Material

The absorbent core 28 comprises one or more area(s) 26 which is/are substantially free of absorbent material. By "substantially free" it is meant that in each of these areas the basis weight of the absorbent material is at least less than 25%, in particular less than 20%, less than 10%, of the average basis weight of the absorbent material in the rest of the core. In particular there can be no absorbent material in these areas. Minimal amount such as involuntary contaminations with absorbent material that may occur during the making process are not considered as absorbent material. The top side 16 of the core wrap is attached to the bottom side 16' of the core wrap by core wrap bond(s) 27 through these area(s) 26 substantially free of absorbent material. When the absorbent material swells upon absorbing a liquid, the core wrap bond remains at least initially attached in the substantially material free area(s) 26. In some embodiments, the core wrap bond in the area 26 serves as a continuous permanent seal 410, forming a portion of the chamber periphery. The absorbent material swells in the rest of the core when it absorbs a liquid, so that the core wrap may form one or more channel(s) 26 along the area(s) 26 substantially free of absorbent material comprising the core wrap bond. These channels 26 can be three dimensional and can serve to distribute an insulting fluid along their length to a wider area of the core. This may provide a quicker fluid acquisition speed and a better utilization of the absorbent capacity of the core. The channels 26 can also provide a deformation of an overlying layer such as an acquisition-distribution system layer 54 and provide corresponding ditches in the overlying layer. It is not excluded that the absorbent core may comprise other area(s) substantially free of absorbent material but without a core wrap bond, but these non-bonded areas will typically not form a channel when wet.

Figure 5:
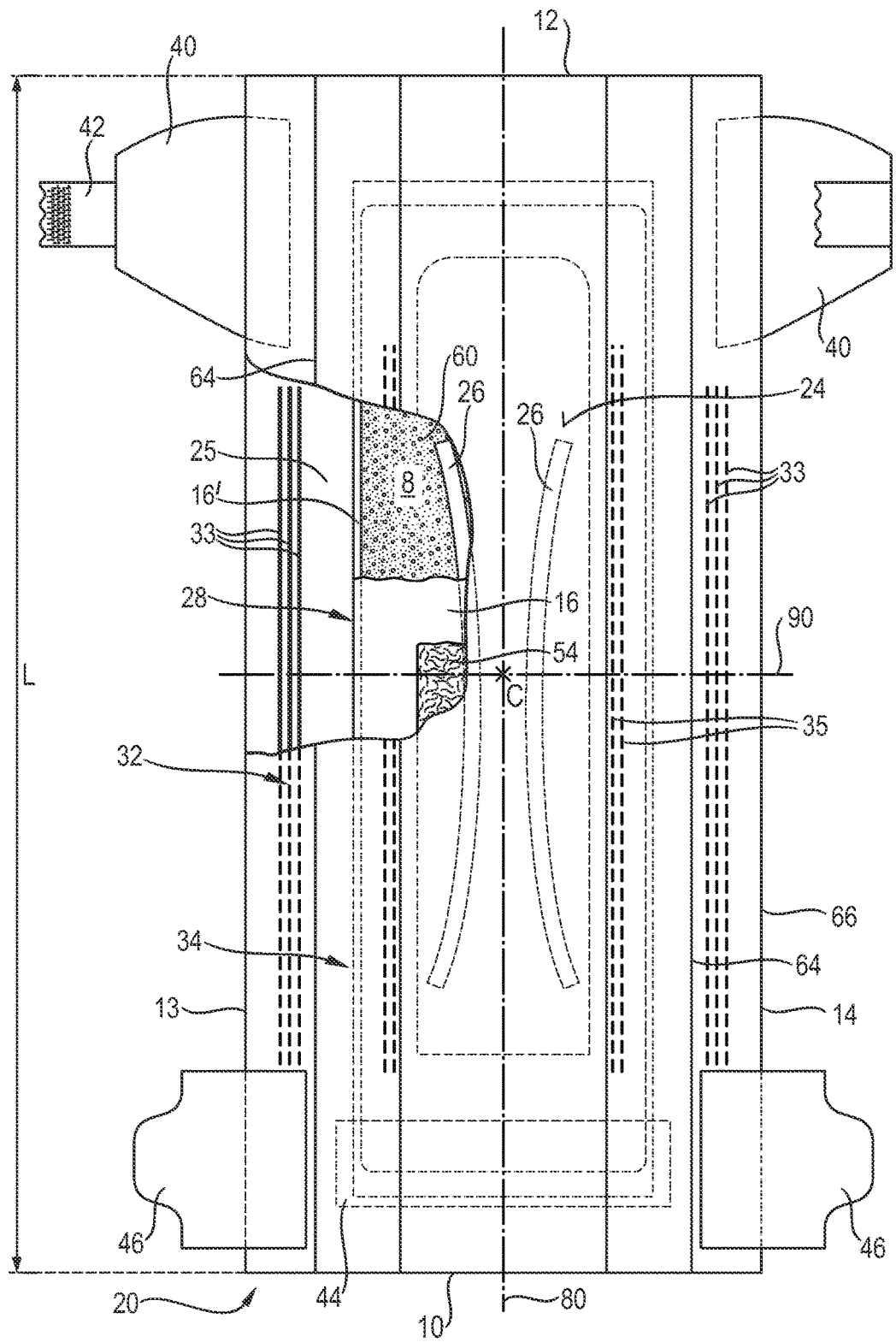
FIG. 5 is a plan view of an exemplary absorbent article.

The substantially material free area(s) 26 may be present within the crotch region of the article, in particular at least at the same longitudinal level as the crotch point C', as represented in FIGS. 1, 5 by the longitudinally extending areas substantially free of absorbent material 26. The absorbent core may comprise one or more pairs of areas substantially free of absorbent material symmetrically arranged relative to the longitudinal axis 80'.

The area(s) 26 substantially free of absorbent material may extend substantially longitudinally, which means typically that each area extends more in the longitudinal direction than in the transverse direction, and typically at least twice as much in the longitudinal direction than in the transverse direction (as measured after projection on the respective axis). The area(s) 26 substantially free of absorbent material may have a length projected on the longitudinal axis 80' of the core that is at least 10% of the length L" of the absorbent core, in particular from 20% to 80%. It may be advantageous that at least some or all of the area(s) 26 are not completely or substantially completely transversely oriented channels in the core.

Swelling Chambers

Figure 6:
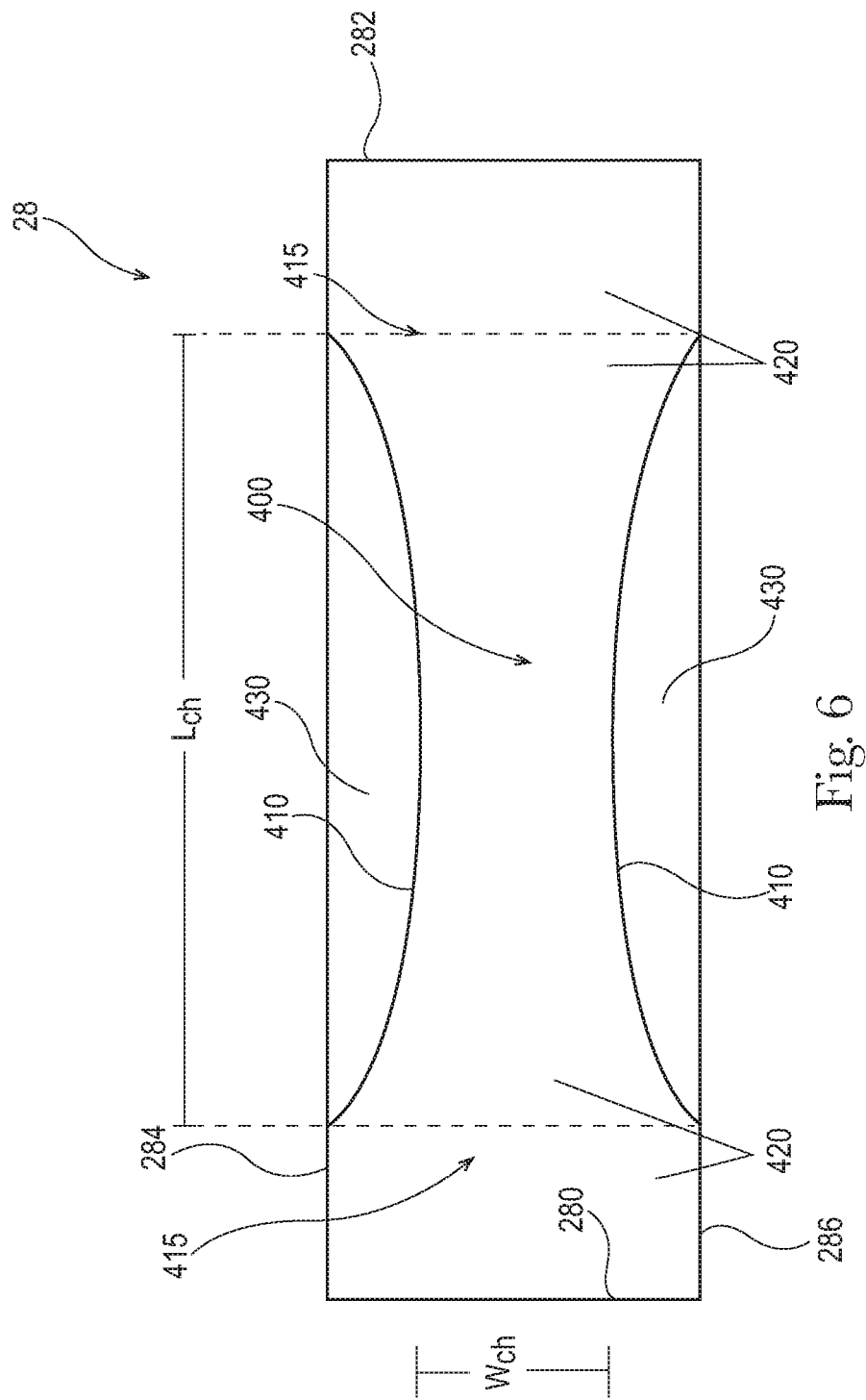
FIGS. 6-6D illustrate exemplary absorbent cores having tube-shaped swelling chambers as described herein.
Figure 6A:
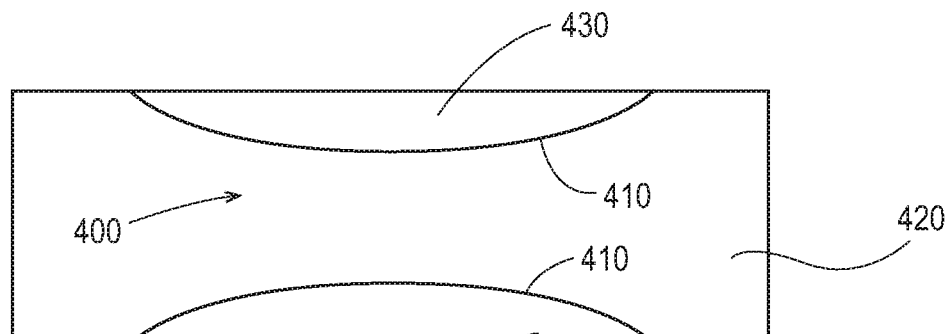
Figure 6B:
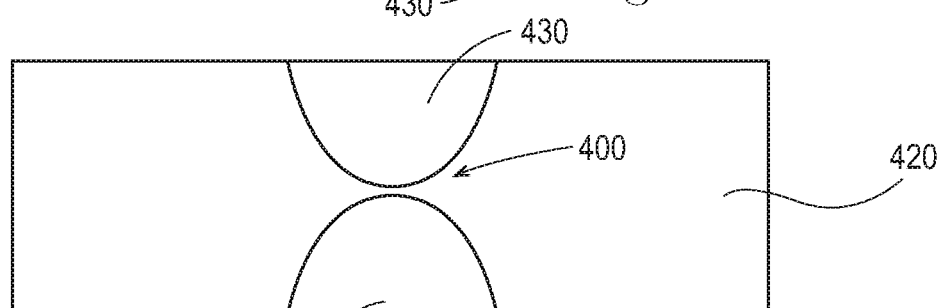
Figure 6C:
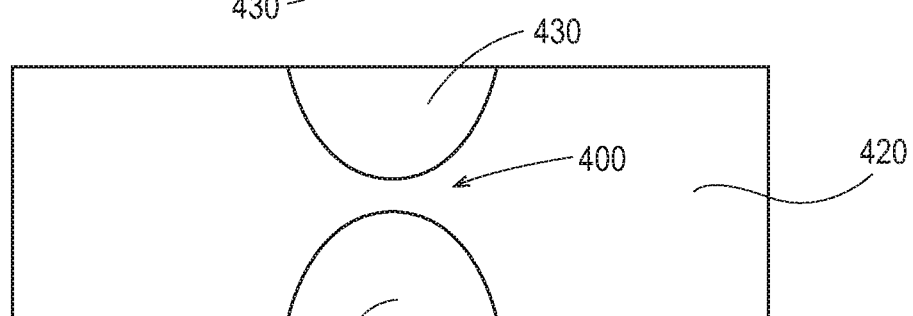
Figure 6D:
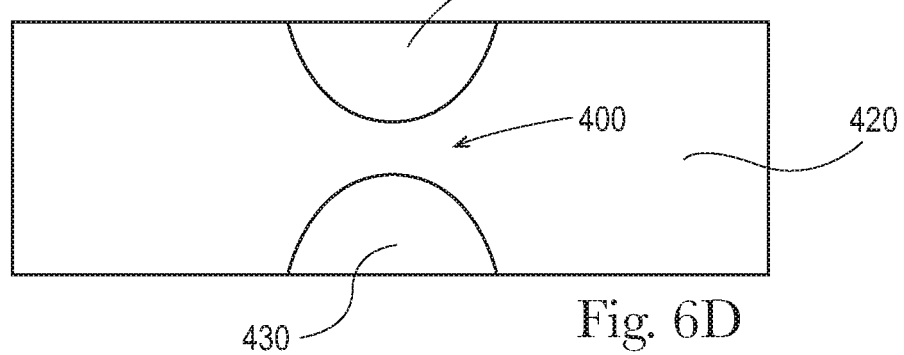

The absorbent core may comprise one or more swelling chambers 400. The swelling chamber may be tube-shaped as shown in FIGS. 6-6D. The swelling chamber is a portion of the absorbent core containing absorbent material, such as superabsorbent polymer, and being delimited by a plurality of continuous permanent seals 410. In nonlimiting examples, the swelling chamber is delimited by two continuous permanent seals 410. The seals 410 join the top 16 and bottom 16' layers of the core wrap. The seals 410 may be void of absorbent material (i.e., the seals may be in the form of channels 26). The seals 410 separate absorbent material internal chamber zones 420 from external zones 430. The external zones 430 may be free from absorbent material, may comprise absorbent material which is immobilized in its wet state, or in some cases, may comprise mobile absorbent material which does not flow in the same manner as in the internal chamber zone. In this way, wet absorbent material within the chamber may flow within the internal chamber zones 420 but be prevented from entering the external zones 430.

The external zones may be disposed adjacent to a side of the core (e.g., 284, 286). In certain embodiments, the external zone is disposed adjacent to an edge of the absorbent material deposition area 8, which edge may be set apart from a side of the core as illustrated for example in FIG. 1. In nonlimiting examples, one or more continuous permanent seals delimiting the swelling chamber may extend to a side of the absorbent material deposition area, or may be within 10 mm or less, or 5 mm or less, or 2 mm from the most proximate side. In some embodiments, the permanent seals 410 delimiting the swelling chamber do not extend to a side of the core. In further examples, the permanent seals may extend to some but not all sides, as shown for example in FIG. 6.

The swelling chamber may be open on one or more ends 415, meaning the plurality of permanent bonds are discrete (i.e., disconnected) at said end. For clarity, the ends are marked by imaginary lines on FIG. 6. FIGS. 6-6D show embodiments having chambers with open ends. In some embodiments, one or more chamber ends 415 may be closed. In such embodiments, the closed end may be formed by one continuous permanent bond that forms said end or by the joining of multiple permanent seals at such end to close the chamber. In nonlimiting examples, the chamber may be open on one end and closed on another end, such as an opposing end.

The continuous permanent seals may be formed by a suitable bonding means, including but not limited to adhesive, ultrasonic bonding, heat bonding, pressure bonding, mechanical bonding or combinations thereof.

In certain embodiments, one or more continuous permanent seals are longitudinally extending, having a longitudinal dimension that exceeds the transverse dimension, and typically at least twice as much in the longitudinal direction than in the transverse direction (as measured after projection on the respective axis). It is also contemplated that one or more permanent seals are transversely-extending, having a transverse dimension that exceeds the longitudinal dimension, typically by at least twice the longitudinal dimension. The permanent seals may have any suitable width, provided the seal sufficiently serves to prevent absorbent material, in particular superabsorbent polymer material, from passing from the internal chamber zone 420 into the external zones 430 in the area where the seal is present.

The tube-shaped swelling chamber may have a length to width aspect ratio of about 5 or less, or about 3 or less, or about 2.5 or less. The length of the chamber ($L_{CH}$) is measured as the greatest distance between end points of permanent seals in the major dimension of the chamber (i.e., length would be the maximum longitudinal distance if the chamber is longitudinally extending), and width ($W_{CH}$) is the average distance between two permanent seals in the direction perpendicular to the length. The width of the chamber may be from about 20% to about 50% of the width of the core, reciting for said range every 5% increment therein. In nonlimiting examples, the width of the chamber is from about 2 cm to about 5 cm, reciting for said range every 0.5 cm increment therein. Additionally, the swelling chamber has an area that is less than the area of the core. In nonlimiting examples, the area of the core is at least about 1.5 times greater, or at least about 2 times greater, or from about 1 times to about 3 times greater than the area of the swelling core.

Permanent seals, or portions thereof, may be substantially straight. Permanent seals, or portions thereof, may be disposed at an angle with respect to the longitudinal axis and/or with respect to the transverse axis. Permanent seals may be curved or comprise curved portions. The permanent seals may form walls that are concave with respect to the longitudinal axis of the core. In certain embodiments, two permanent seals may be substantially parallel and/or may be substantially mirror images for a least a portion of their respective lengths. In nonlimiting examples, two permanent seals are substantially parallel and/or substantially mirror images for at least 25% of the length of the shortest of the two seals, or at least 50% of the length of the shortest of the two seals, or from about 25% to about 100% of the length of the shortest of the two seals, reciting for said range every 5% increment therein.

Fibrous Adhesive Material 51

The absorbent core may optionally comprise a fibrous adhesive material, in particular a microfiber glue, to further immobilize a portion of the absorbent material within the core. The fibrous adhesive material may be a fibrous thermoplastic adhesive material 51, which may immobilize SAP in the dry and wet state. Suitable fibrous thermoplastic adhesive materials are disclosed in U.S. application. Ser. No. 13/491,642 to Rosati. In some nonlimiting examples, a fibrous adhesive material may be utilized in a permanent seal.

However, it is also contemplated that in certain embodiments, the absorbent cores enable SAP immobilization at a sufficiently high degree that a fibrous thermoplastic adhesive material is not needed. In these embodiments, the absorbent cores, or portions of the absorbent cores, of the invention do not contain a fibrous thermoplastic adhesive material.

Auxiliary Glue 71, 72

The absorbent core of the invention may further comprise an auxiliary glue present on the inner surface of the top side and/bottom side of the absorbent core in one or more portions of the absorbent core, in particular to help immobilizing the SAP within the core wrap in the external zone, to ensure integrity of the core wrap and/or to form the bond attaching the bottom side of the core wrap to the top side of the core wrap to form a permanent seal 410.

Example of glues are based on an adhesive polymer such SIS (Styrene-Isoprene-Block Co-Polymer), SBS (Styrene-Butadiene-Block Co-polymer) or mPO (metalocine Polyolefine). The glue may also comprise a tackifier such as a hydrogenated hydrocarbon resin, as well as an oil and an antioxidant. Hydrogenated hydrocarbon resins are made from mixed aromatic/aliphatic resins which are subsequently selectively hydrogenated to produce a wide range of materials with low color, high stability and broad compatibility. Examples of commercially available adhesives are available as HL1358LO and NW1286 (both from HB Fuller) and DM 526 (from Henkel).

This so-called auxiliary glue 71, 72 can be applied on the inner surface of the top side and/or the bottom side of the core wrap. The auxiliary glue may be any conventional glue used in the field, in particular hotmelt glue. The auxiliary glue may be applied on the top side and/or the bottom side of the core wrap in an average amount ranging from 2 gsm to 20 gsm, more particularly from 4 gsm to 10 gsm. The auxiliary glue may be uniformly applied, or discontinuously, in particular as a series of stripes regularly spaced and longitudinally oriented, for example a series of auxiliary glue stripes of about 1 mm width spaced from each other by a distance ranging from 1 mm to 3 mm. The auxiliary glue may help forming the core wrap bond if sufficient pressure and glue is applied within the material free area 26 to attach both sides of the core wrap. The auxiliary glue layer may be applied to the inner surface of the bottom side, the inner surface of the top side, or both inner surfaces of the core wrap.

Absorbent Articles

The absorbent cores of the invention may be disposed in absorbent articles, e.g. as discussed and further illustrated in the form of a baby diaper 20 in FIG. 5. FIG. 5 is a plan view of the exemplary diaper 20, in a flattened state, with portions of the structure being cut-away to more clearly show the construction of the diaper 20. This diaper 20 is shown for illustration purpose only as the invention may be used for making a wide variety of diapers or other absorbent articles.

The absorbent article comprises a liquid permeable topsheet 24, a liquid impermeable backsheet 25, and an absorbent core 28 between the topsheet 24 and the backsheet 25. An optional acquisition-distribution system 54 is represented on FIG. 5, which also shows other typical taped diaper components such as a fastening system comprising adhesive tabs 42 attached towards the back edge of the article and cooperating with a landing zone 44 on the front of the article, barrier leg cuffs 34 and elasticized gasketing cuffs 32 joined to the chassis of the absorbent article, typically via the topsheet and/or backsheet, and substantially planar with the chassis of the diaper. The absorbent article may also comprise other typical elements, which are not represented, such as a back elastic waist feature, a front elastic waist feature, transverse barrier cuff(s), a lotion application, graphics, wetness indicators, etc.

The absorbent article 20 comprises a front edge 10, a back edge 12, and two side (longitudinal edges) 13, 14. The front edge 10 of the article is the edge which is intended to be placed towards the front of the user when worn, and the back edge 12 is the opposite edge of the article. The absorbent article may be notionally divided by a longitudinal axis 80 extending from the front edge to the back edge of the article and dividing the article in two substantially symmetrical halves relative to this axis, with article placed flat and viewed from above as in FIG. 5. The length L of the article can be measured along the longitudinal axis 80 from front edge 10 to back edge 12. The article comprises a crotch point C defined herein as the point placed on the longitudinal axis at a distance of two fifth (2/5) of L starting from the front edge 10 of the article 20. The width of the article for a diaper application at the crotch point may in particular be of from 50 mm to 300 mm, or from 80 mm to 250 mm. For adult incontinence products the width may go up to 450 mm.

The crotch region can be defined as the region of the diaper longitudinally centered at the crotch point C and extending towards the front and towards the back of the absorbent article by a distance of one fifth of L (L/5) in each direction. A front region and a back region can be defined as the remaining portions of the diapers placed respectively towards the front and the back edges of the article.

The topsheet 24, the backsheet 25, the absorbent core 28 and the other article components may be assembled in a variety of known configurations, in particular by gluing or heat embossing. Exemplary diaper configurations are described generally in U.S. Pat. Nos. 3,860,003, 5,221,274, 5,554,145, 5,569,234, 5,580,411, and 6,004,306. The absorbent article is preferably thin. The caliper at the crotch point C of the article may be for example from 3.0 mm to 12.0 mm, in particular from 4.0 mm to 10.0 mm, as measured with the Absorbent Article Caliper Test described herein.

For most absorbent articles, the liquid discharge occurs predominately in the front half of the article, in particular for diaper. The front half of the article (as defined by the region between the front edge and a transversal line 90 placed at a distance of half L from the front or back edge may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article. As the absorbent article of the present invention has the ability to move the gel away from the crotch during use an execution may even have 100% of the SAP in the front half of the absorbent article, or have up to 100% in the crotch region of the absorbent article.

The absorbent article may have an acquisition time for the first gush of less than 30 s, preferably less than 27 s, as measured according to the Flat Acquisition test method set out in WO2012/174026A1. This acquisition time may be in measured in particular on a baby diaper which is designated for wearers having a weight in the range of 8 to 13 kg±20% (such as Pampers Active Fit size 4 or other Pampers baby diapers size 4, Huggies baby diapers size 4 or baby diapers size 4 of most other tradenames).

Topsheet 24

The topsheet 24 is the layer of the absorbent article that is destined to be in contact with the wearer's skin. The topsheet 24 can be joined to the backsheet 25, the core 28 and/or any other layers as is known in the art. Usually, the topsheet 24 and the backsheet 25 may be joined directly to each other on or close to the periphery of the article and are indirectly joined together in other locations by directly joining them to one or more other elements of the article 20. The topsheet may be attached to an underlying layer 54, which may be an acquisition and/or distribution layer, by any conventional means, in particular gluing, mechanical or heat bonding and combinations thereof. The topsheet may in particular be attached directly or indirectly to the acquisition-distribution system 54 (if present) in the area where the ditches are formed. This may provide or help the formation of secondary ditches at the surface of the article.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet 24 may be coated with a lotion as is known in the art. Examples of suitable lotions include those described in U.S. Pat. Nos. 5,607,760, 5,609, 587, 5,635,191, 5,643,588, 5,968,025 and 6,716,441. The topsheet 24 may also include or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504, assigned to BBA NONWOVENS SIMPSONVILLE. WO2011/163582 also discloses suitable colored topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet. Typical diaper topsheets have a basis weight of from about 10 to about 28 gsm, in particular between from about 12 to about 18 gsm but other basis weights are possible.

Backsheet 25

The backsheet 25 is generally that portion of the absorbent article 20 which forms the majority of the external surface of the article when worn by the user. The backsheet is positioned towards the bottom side of the absorbent core and prevents the exudates absorbed and contained therein from soiling articles such as bedsheets and undergarments. The backsheet 25 is typically impermeable to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 25 may be joined to the topsheet 24, the absorbent core 28 or any other element of the diaper 20 by any attachment means known in the art. Suitable attachment means are described above with respect to means for joining the topsheet 24 to other elements of the article 20. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minn. and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Acquisition Distribution System 54

The absorbent article may further comprise an acquisition-distribution system that can serve to acquire and distribute the fluid, as illustrate by layer 54 in the Figures. The acquisition-distribution system may comprise one or more layers which may be present between the topsheet 24 and the absorbent core 28, as represented in the Figures, but may be also between the backsheet 25 and the absorbent core 28, or both. The acquisition-distribution system 54 may be at least partially bonded to the top side or the bottom side of the core wrap in the area(s) substantially free of absorbent material. The formation of the channel 26 in the absorbent core as the absorbent material swells may thus provide of one or more corresponding ditches in the at least one of the layers of the acquisition-distribution system 54.

The acquisition-distribution system layer(s) may be of any kind such as nonwoven, a woven material or even loose fibers. The layers may in particular be of the type known in the art for acquisition layers and/or distribution layers. Typical acquisition and/or distribution layers do not comprise SAP as this may slow the acquisition and distribution of the fluid, but an acquisition-distribution system may also comprise SAP if some fluid retention properties are wished. The prior art discloses many type of acquisition and/or distribution layers that may be used, see for example WO2000/59430 (Daley), WO95/10996 (Richards), U.S. Pat. No. 5,700,254 (McDowall), WO02/067809 (Graef).

A distribution layer can spread an insulting fluid liquid over a larger surface within the article so that the absorbent capacity of the core can be more efficiently used. Typically distribution layers are made of a nonwoven material based on synthetic or cellulosic fibers and having a relatively low density. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer may also be a material having a water retention value of from 25 to 60, preferably from 30 to 45, measured as indicated in the procedure disclosed in U.S. Pat. No. 5,137,537. The distribution layer may typically have an average basis weight of from 30 to 400 g/m$^2$, in particular from 100 to 300 g/m$^2$.

The distribution layer may comprise a fibrous layer. The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance to the first absorbent layer against the compression in the product packaging or in use conditions, e.g. under a baby's weight. This provides the core with a higher void volume, permeability and liquid absorption, and hence reduced leakage and improved dryness.

Exemplary chemically cross-linked cellulosic fibers suitable for a distribution layer are disclosed in U.S. Pat. Nos. 5,549,791, 5,137,537, WO9534329 or US2007/118087. Exemplary cross-linking agents include polycarboxylic acids such as citric acid and/or polyacrylic acids such as acrylic acid and maleic acid copolymers. In some embodiments, the formation of the channel 26 in the absorbent core as the absorbent material swells provides of one or more corresponding ditches in the distribution layer.

The absorbent article may also comprise an acquisition layer, whose function can be to quickly acquire the fluid away from the topsheet so as to provide a good dryness for the wearer. Such an acquisition layer is typically placed directly under the topsheet. The absorbent article may also then comprise a distribution layer typically placed between the acquisition layer and the absorbent core.

The acquisition layer may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material. Further useful non-wovens are described in U.S. Pat. Nos. 6,645, 569, 6,863,933 (both to Cramer), U.S. Pat. No. 7,112,621 (Rohrbaugh), and co patent applications US2003/148684 to Cramer et al. and US2005/008839 (both to Cramer).

Such an acquisition layer may be stabilized by a latex binder, for example a styrene-butadiene latex binder (SB latex). Processes for obtaining such latexes are known, for example, from EP 149 880 (Kwok) and US 2003/0105190 (Diehl et al.). In certain embodiments, the binder may be present in the acquisition layer in excess of about 12%, about 14% or about 16% by weight. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-22.5 gsm high wet strength made of cellulose fibers from supplier Havix.

If an acquisition layer is present, it may be advantageous that this acquisition layer is larger than or least as large as an underlying distribution layer in the longitudinal and/or transversal dimension. In this way the distribution layer can be deposited on the acquisition layer. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer larger than the distribution layer allows to directly glue the acquisition layer to the storage core (at the larger areas). This can give increased patch integrity and better liquid communication.

However, it is also contemplated that in certain embodiments, the absorbent cores enable active liquid distribution at a sufficiently high degree that one or more, or all, layers of an acquisition-distribution system are not needed. In these embodiments, the absorbent article comprising the absorbent cores of the invention do not contain an acquisition layer and/or do not contain a distribution layer.

Fastening System 42, 44

The absorbent article may include a fastening system, for example as is known in taped diapers. The fastening system can be used to provide lateral tensions about the circumference of the absorbent article to hold the absorbent article on the wearer as is typical for taped diapers. An inclined fastening system can also provide tension around the legs of the wearer. This fastening system is not necessary for (training) pant articles since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499, 978, 5,507,736, and 5,591,152.

Barrier Leg Cuffs 34

The absorbent article may comprise a pair of barrier leg cuffs 34 and/or gasketing cuffs 32. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier leg cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion.

The barrier leg cuffs 34 can be formed from a piece of material, typically a nonwoven, which is partially bonded to the rest of the article so that a portion of the material, the barrier leg cuffs, can be partially raised away and stand up from the plane defined by the topsheet when the article is pulled flat as shown e.g. in FIG. 5. The barrier leg cuffs can provide improved containment of liquids and other body exudates approximately at the junction of the torso and legs of the wearer. The barrier leg cuffs extend at least partially between the front edge and the back edge of the diaper on opposite sides of the longitudinal axis and are at least present at the longitudinal position of the crotch point (C). The barrier leg cuffs are delimited by a proximal edge 64 joined to the rest of the article, typically the topsheet and/or the backsheet, and a free terminal edge 66, which is intended to contact and form a seal with the wearer's skin. The barrier leg cuffs are joined at the proximal edge 64 with the chassis of the article by a bond 65 which may be made for example by gluing, fusion bonding or combination of known bonding means. The bond 65 at the proximal edge 64 may be continuous or intermittent. The side of the bond 65 closest to the raised section of the barrier leg cuffs 32 delimits the proximal edge 64 of the standing up section of the leg cuffs.

The barrier leg cuffs 34 can be integral with the topsheet or the backsheet, or more typically be formed from a separate material joined to the rest of the article. Typically the material of the barrier leg cuffs may extend through the whole length of the diapers but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge 66 to provide a better seal.

In addition to the barrier leg cuffs 34, the article may comprise gasketing cuffs 32 joined to the chassis of absorbent article, in particular the topsheet and/or the backsheet and may be placed externally relative to the barrier leg cuffs. The gasketing cuffs can provide a better seal around the thighs of the wearer. Usually each gasketing leg cuff will comprise one or more elastic string or elastic element comprised in the chassis of the diaper for example between the topsheet and backsheet in the area of the leg openings.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing or pressure bonding. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Method of Making the Article—Relations Between the Layers

The absorbent articles of the invention may be made by any conventional methods known in the art. In particular the articles may be hand-made or industrially produced at high speed. Typically, adjacent layers and components will be joined together using conventional bonding method such as adhesive coating via slot coating or spraying on the whole or part of the surface of the layer, or thermo-bonding, or pressure bonding or combinations thereof. This bonding is exemplarily represented for the bond between the leg cuffs 65 and the topsheet 24, and the auxiliary glues 71, 72 and microfibrous glue 51 on the detail view of the absorbent core on FIG. 4. Other glues or attachments are not represented for clarity and readability but typical bonding between the layers of the article should be considered to be present unless specifically excluded. Adhesives may be typically used to improve the adhesion of the different layers, for example between the backsheet and the core wrap. The glue may be any standard hotmelt glue as known in the art.

The absorbent core and in particular its absorbent material deposition area 8 may advantageously be at least as large and long and advantageously at least partially larger and/or longer than the fibrous layer. This is because the absorbent material in the core can usually more effectively retain fluid and provide dryness benefits across a larger area than the fibrous layer. The absorbent article may have a rectangular SAP layer and a non-rectangular (shaped) fibrous layer. The absorbent article may also have a rectangular (non-shaped) fibrous layer and a rectangular layer of SAP.

EXAMPLES

FIGS. 6-6D are illustrations of suitable tube-shaped swelling chamber designs. These cores have tube-shaped swelling chambers 400, delimited by permanent seals 410 existing between chamber internal zones 420, wherein SAP is flowable, and external zones 430. Dry SAP may be immobilized in the flowable areas using any of the techniques described herein. Wet SAP may flow in the flowable areas but will be prevented from escaping a zone by the permanent seals.

Packages

Figure 7:
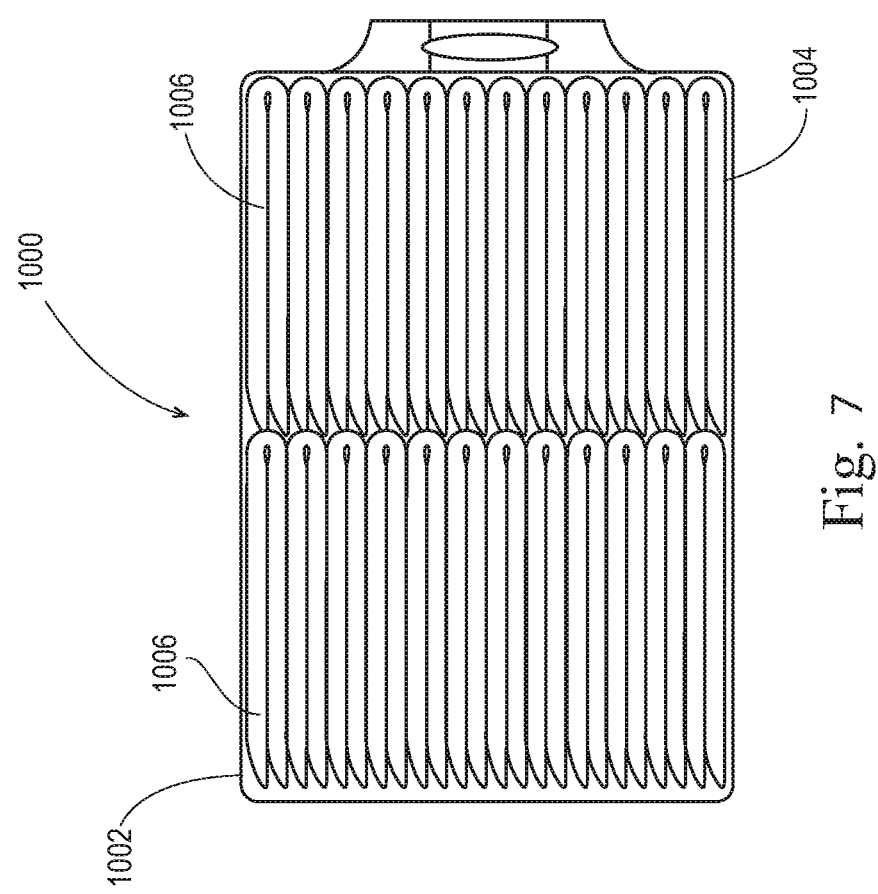
FIG. 7 is an example package comprising a plurality of absorbent articles.

The absorbent articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages. FIG. 7 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

The three-dimensional material may be particularly resilient to compression so that the articles may be compressed to a certain extent in the package. It is believed that the plurality of relatively closely spaced, relatively small, and relatively pillowy three-dimensional projections may act as springs to resist compression and recover once a compressive force is removed, especially in the areas in the vicinity of the channels. Compression recovery is important in nonwoven or other component layers of absorbent articles, because such articles are typically packaged and folded in compressed conditions. Manufacturers of personal care products desire to retain most, if not all of the as-made caliper for aesthetic and performance purposes. Furthermore, without being bound by theory, it is believed that in those embodiments in which the channels are substantially material-free, this may contribute to an unexpected, beneficial improvement in compression recovery as they provide spacing for at some of the three-dimensional projections to nest in during storage and transport in the compressed package state.

The articles of the invention may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Methods. The articles before compression may be typically sampled from the production line between the folding unit and the stack packing unit. The stack height before compression is measured by taking 10 articles before compression and packing, and measuring their stack height as indicated for the In-Bag Stack Height.

Packages of the absorbent articles of the present disclosure may have an In-Bag Stack Height of from 55 mm to 110 mm, preferably from 55 mm to 85 mm. Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For the values shared in the previous sentence, it may be desirable to have an In-Bag Stack Height of greater than 55 mm, or greater than 70 mm, or greater than 75 mm, or greater than 80 mm. Alternatively, packages of the absorbent articles of the present disclosure may have an In-Bag Stack Height of from 70 mm to 110 mm, from 75 mm to 110 mm, from 80 mm to 110 mm, from 80 mm to 105 mm, or from 80 mm to 100 mm, specifically reciting all 0.1 mm increments within the specified ranges and all ranges formed therein or thereby, according to the In-Back Stack Height Test described herein.

Test Methods
Ball Breakthrough (BB) Test

This test determines the ball breakthrough (BB) value of an SAP composition. The BB value is the force (peak load, in grams force) required to rupture a layer of an SAP composition that is swollen in synthetic urine solution, under procedures specified in the test method. BB is a measure of the integrity of a layer of the SAP composition in the swollen state.

Figure 8:
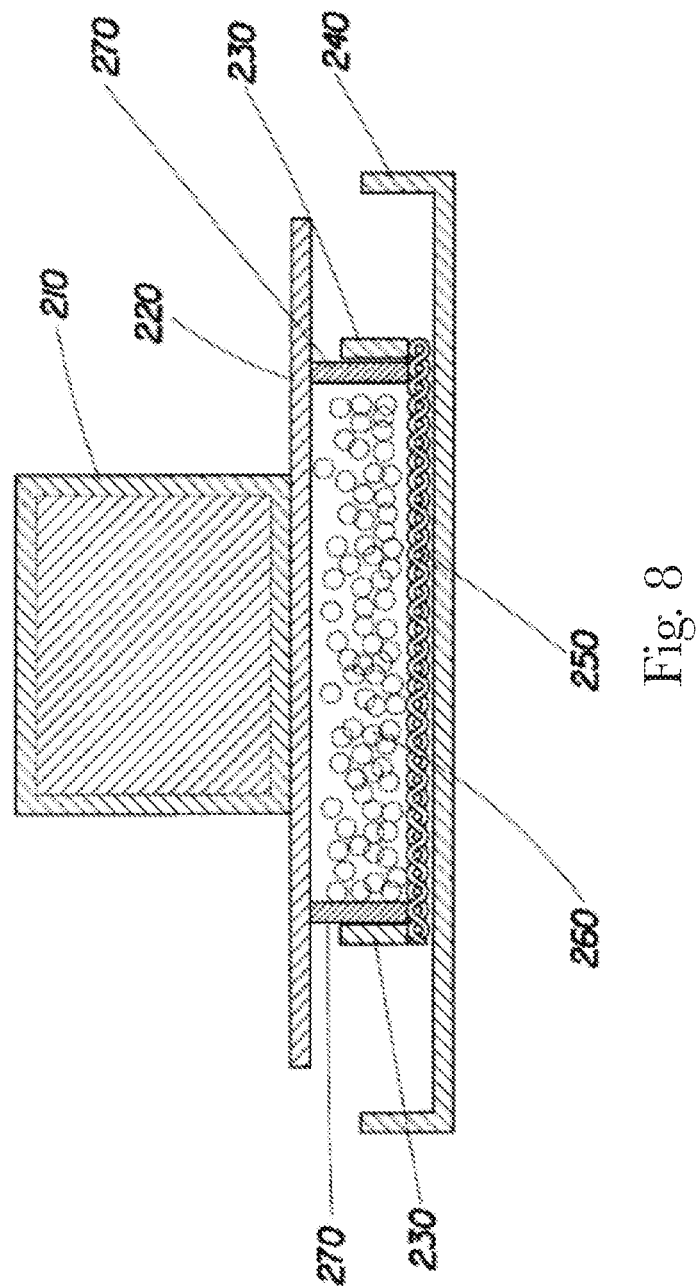
FIG. 8 is a sampling apparatus suitable for use in the BB test method described herein.

A suitable apparatus for BB measurement is shown in FIG. 8. This apparatus comprises an inner cylinder 270 which is used to contain an SAP layer 260, an outer cylinder 230, a Teflon® flat-bottomed tray 240, an inner cylinder cover plate 220, and a stainless steel weight 210. The inner cylinder 270 is bored from a transparent Lexan® rod or equivalent, and has an inner diameter of 6.00 cm (area=28.27 cm$^2$), with a wall thickness of approximately 0.5 cm, and a height of approximately 1.50 cm. The outer-cylinder 230 is bored from a Lexan rod or equivalent, and has an inner diameter that is slightly larger than the outer diameter of the inner-cylinder 270, so that the inner-cylinder 270 fits within the outer-cylinder 230 and slides freely. The outer cylinder 230 has a wall thickness of approximately 0.5 cm, and a height of approximately 1.00 cm. The bottom of the outside-cylinder 230 is faced with a 400 mesh stainless steel screen 250 that is biaxially stretched to tautness prior to attachment. The inner cylinder cover plate 220 is made of glass plate with a thickness of 0.8 cm and a weight of 500 g. The stainless steel weight 210 has a weight of 1700 g. Also used is a circular sheet (not shown) of filter paper (Whatman; 589/1; 90 mm diameter).

Figure 9:
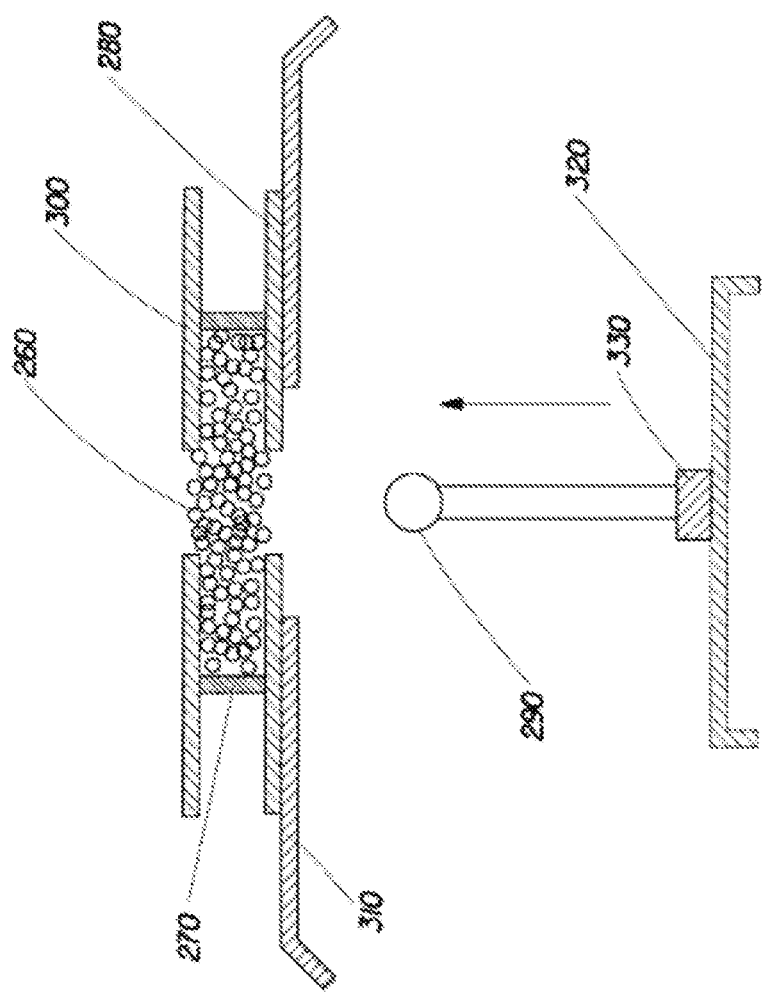
FIG. 9 is a tensile tester suitable for use in the BB test method described herein.

A Tensile Tester with a burst test load cell (available from Intelect-II-STD Tensile Tester, made by Thwing-Albert Instrument Co., Pennsylvania) is used for this test. Referring to FIG. 9, this instrument comprises a force sensing load cell 330 equipped with a polished stainless steel ball-shaped probe 290, a moving crosshead 320, a stationary crosshead 310, a circular lower platen 280, and an upper clamping platen 300 that is used to clamp the sample 260 pneumatically. The lower clamp platen 280 is mounted on the stationary crosshead 310. Both lower clamp platen 280 and upper clamp platen 300 have a diameter of 115 mm, a thickness of 2.9 mm, and a circular opening 18.65 mm in diameter. The polished stainless steel ball-shaped probe 290 has a diameter of 15.84 mm. During the BB test procedure, the moving crosshead 320 moves up, causing the probe 290 to contact and penetrate the sample 260. When the probe 290 penetrates the sample 260, the test is considered complete, and the appropriate data are recorded.

Referring to the Sampling Apparatus depicted in FIG. 8, a sheet of filter paper is placed into and centered within the flat-bottomed tray 240. The inner cylinder 270 is inserted into the outside-cylinder 230. A 1.0 g sample of SAP composition is added to the inner cylinder 270 and dispersed evenly on the 400 mesh stainless steel screen 250. The assembled cylinders with SAP are transferred to the flat-bottomed tray 240 onto the filter paper, and inner-cylinder cover plate 220 is positioned onto inner-cylinder 270. A 30.0 mL aliquot of synthetic urine solution is poured into the flat-bottomed tray 240. Care should be taken not to pour the synthetic urine solution into the tray slowly enough that it may be absorbed unevenly by the SAP. To avoid pouring too slowly, the synthetic urine solution may, e.g., be poured using an automatically dispensing pipette, e.g. Multipipette® Stream (available from Eppendorf, Hamburg, Germany), set to pour at a rate of 30 ml/8.75 sec (3.43 ml/sec). The synthetic urine solution passes through the filter paper and through the stainless screen and is absorbed by the absorbent polymer composition 260. Five minutes after the all of the fluid is completely absorbed from the tray by the SAP, the stainless steel weight 210 is placed onto the inner-cylinder cover plate 220. After an additional 25 minutes, stainless steel weight 210 and inner cylinder cover plate 220 are removed. For the procedure to be valid, all of the synthetic urine solution must be absorbed by the absorbent polymer composition at this point. The assembled cylinders with swelled SAP are removed from flat-bottomed tray 240, and upper clamping platen 300 is placed onto the inner-cylinder 270. The assembled cylinders with swelled SAP are inverted 180°, so that upper clamping platen 300 is now on the bottom of the inner cylinder 270, and outer cylinder 230 is carefully removed from the assembly of cylinders, leaving the swollen SAP layer 260 sitting on top of upper clamping platen 300, and not leaving it on the stainless steel screen 250. The inner-cylinder 270 with the layer of swollen absorbent polymer 260 is immediately transferred to the Burst Tester for measurement of the BB.

Referring to the Burst Tester depicted in FIG. 9, inner-cylinder 270 with the swollen absorbent polymer layer 260 is centrally positioned on lower clamp platen 280 and is fixed pneumatically with upper clamping platen 300. The measurement is performed using a break sensitivity of 10.00 g and a test speed of 5.00 inch/minute. The measurement is initiated and the crosshead 320 moves up until polished stainless steel ball-shaped probe 290 penetrates absorbent material gel layer 260. After a sample burst is registered, moving crosshead 320 returns to start position. The BB is expressed as peak load in grams force. The average of three determinations is reported as the BB for the absorbent polymer composition.

Absorption Against Pressure (AAP) Test

The AAP is measured according to EDANA method WSP 442.2-02. For purposes of the present disclosure, this method may also be used to measure the AAP of SAP having more than 0.1% SAP particles smaller than 45 microns, and in order to measure AAP, SAP may be extracted from an absorbent core and then the EDANA test be performed.

Dry Absorbent Core Caliper Test

This test may be used to measure the caliper of the absorbent core (before use i.e. without fluid loading) in a standardized manner at the crotch point C' of the core or any other point.

Equipment: Mitutoyo manual caliper gauge with a resolution of 0.01 mm—or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft and potentially forces of a spring) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.
Stopwatch: Accuracy 1 second
Sample preparation: The core is conditioned at least 24 hours as indicated above.

Measurement procedure: The core is laid flat with the bottom side, i.e. the side intended to be placed towards the backsheet in the finished article facing down. The point of measurement (e.g. the crotch point C corresponding to this point in the finished article) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as per the Dry Absorbent Core Caliper Test described above, the difference being that the caliper of the finished absorbent article is measured instead of the caliper of the core. The point of measurement may be the intersection of the longitudinal axis (80) and transversal axis (90) of the absorbent article or the crotch point C of the article. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the area of measurement.

In-Bag Stack Height Test

The In-Bag stack height of a package of absorbent articles is determined as follows: Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure: Absorbent article packages are equilibrated at 23±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent article counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core comprising absorbent material disposed in an absorbent material deposition area and enclosed in a core wrap, wherein the core wrap comprises a liquid permeable substrate layer and the absorbent material comprises from about 87% to about 100% of superabsorbent polymer by weight of the absorbent material, the absorbent core further comprising a tube-shaped swelling chamber, the tube-shaped swelling chamber having a length to width aspect ratio of less than or equal to about 5:1;

wherein the area of the core is at least twice the area of the swelling chamber, and the core contains a water responsive immobilizing agent to immobilize the superabsorbent polymer prior to water insult; and wherein the tube-shaped swelling chamber is a portion of the absorbent core containing superabsorbent polymer that is delimited by a plurality of continuous permanent seals that each join together a top substrate layer and a bottom substrate layer of the core wrap and prevent superabsorbent polymer from moving across the seals, wherein at least two continuous permanent seals are longitudinally-extending and void of absorbent material wherein the chamber comprises a first chamber end at a first longitudinal position and a second chamber end at a second longitudinal position, wherein the first chamber end of the tube-shaped swelling chamber is closed by joining two or more of the continuous permanent seals together at the first chamber end and the second chamber end comprises an open end such that the plurality of continuous permanent seals are not joined to one another at the second longitudinal position, and wherein at the open end, at least one of the two or more of the continuous permanent seals each extend to a longitudinal edge of the absorbent material deposition area.

2. The absorbent core of claim 1, wherein the aspect ratio is less than or equal to about 2.5:1.

3. The absorbent core of claim 1, wherein the water responsive immobilizing agent is selected from a water soluble adhesive, a frangible pocket sealed with water responsive bonds, or combinations thereof.

4. The absorbent core of claim 1, further comprising two continuous permanent seals.

5. The absorbent core of claim 4, wherein the two continuous permanent seals are substantially parallel for a least a portion of their length.

6. The absorbent core of claim 5, wherein the width of the tube-shaped swelling chamber, being the average distance between the two permanent continuous seals is from about 20% to about 50% of the core width.

7. The absorbent core of claim 5, wherein the width of the swelling chamber, being the average distance between the two continuous permanent seals is from about 2 cm to about 5 cm.

8. The absorbent core of claim 1, wherein the liquid permeable substrate layer of the core wrap is selected from the group consisting of: a nonwoven, a woven, an apertured film, a mesh, a paper, and combinations thereof.

9. The absorbent core of claim 8, wherein the liquid permeable substrate layer has a basis weight from about 8 gsm to about 25 gsm.

10. The absorbent core of claim 8, wherein the liquid permeable substrate layer has a basis weight of about 60 gsm or more.

11. The absorbent core of claim 10, wherein the liquid permeable substrate layer is elastomeric.

12. The absorbent core of claim 1, wherein the core comprises from about 5 g to about 25 g of superabsorbent polymer.

13. The absorbent core of claim 1, wherein the superabsorbent polymer has a value of absorption against pressure (AAP) of about 15 g/g or more.

14. The absorbent core of claim 1, wherein the superabsorbent polymer has an AAP of about 45 g/g or less.

15. The absorbent core of claim 1, wherein the superabsorbent polymer has a value of ball breakthrough from 0 gf to about 50 gf as measured with a Ball Breakthrough Test Method.

16. The absorbent core of claim 1 wherein the plurality of continuous permanent seals separate the tube-shaped swelling chamber from an external zone, and wherein the external zone is substantially free of superabsorbent polymer.

* * * * *